United States Patent [19]

Pasula

[11] Patent Number: 4,788,155

[45] Date of Patent: Nov. 29, 1988

[54] METHOD AND APPARATUS FOR MEASURING THE DEGREE OF REACTION BETWEEN A FOREIGN ENTITY AND A SUBJECT'S BLOOD CELLS

[76] Inventor: Mark J. Pasula, 369 NE. 116 St., Miami, Fla. 33161

[21] Appl. No.: 913,940

[22] Filed: Oct. 1, 1986

Related U.S. Application Data

[63] Continuation-in-part of Ser. No. 547,767, Nov. 1, 1983, Pat. No. 4,614,722, and Ser. No. 902,313, Aug. 28, 1986.

[51] Int. Cl.$^4$ ..................... G01N 33/566; C12Q 1/02
[52] U.S. Cl. .................................... 436/501; 436/63; 436/519; 436/520; 436/522; 435/29; 435/7; 324/71.2
[58] Field of Search ................. 436/501, 513, 519, 63, 436/520, 522; 424/91; 324/71.1, 71.2; 377/10, 11, 12; 435/29, 7

[56] References Cited

U.S. PATENT DOCUMENTS 4,614,722 9/1986 Pasula ................................. 436/501

Primary Examiner—Esther M. Kepplinger
Assistant Examiner—Stephen C. Wieder
Attorney, Agent, or Firm—Roger S. Thompson

[57] ABSTRACT

The invention is directed to a method for the diagnosis of a malady in a subject by observing a degree of reaction between all blood cells: red blood cells, leukocytes and platelets; in the subject's blood with a foreign entity having a predetermined relationship with the malady being diagnosed. The test includes comparing amounts and sizes of red blood cells, leukocytes and/or platelets in a control sample and at least one test sample. The test sample includes a portion of the subject's blood and the foreign entity being tested.

18 Claims, 2 Drawing Sheets

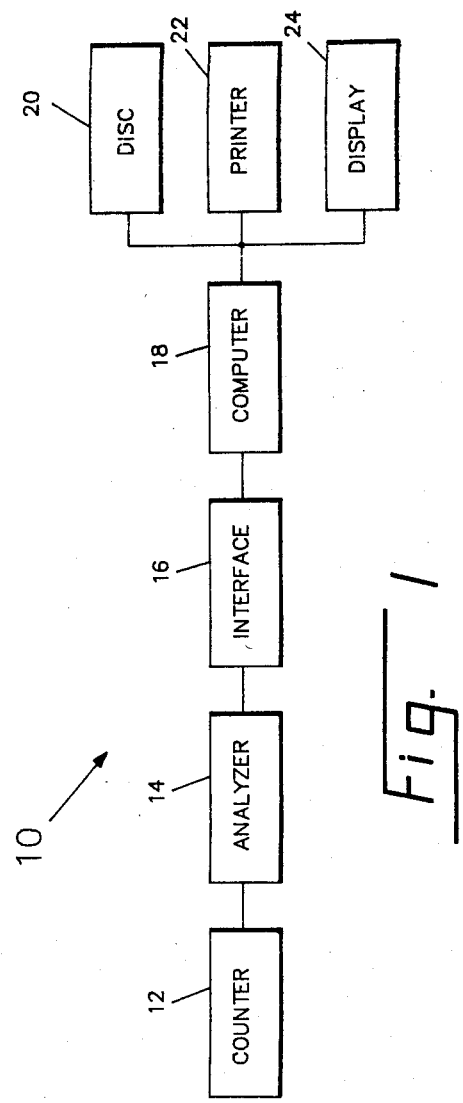

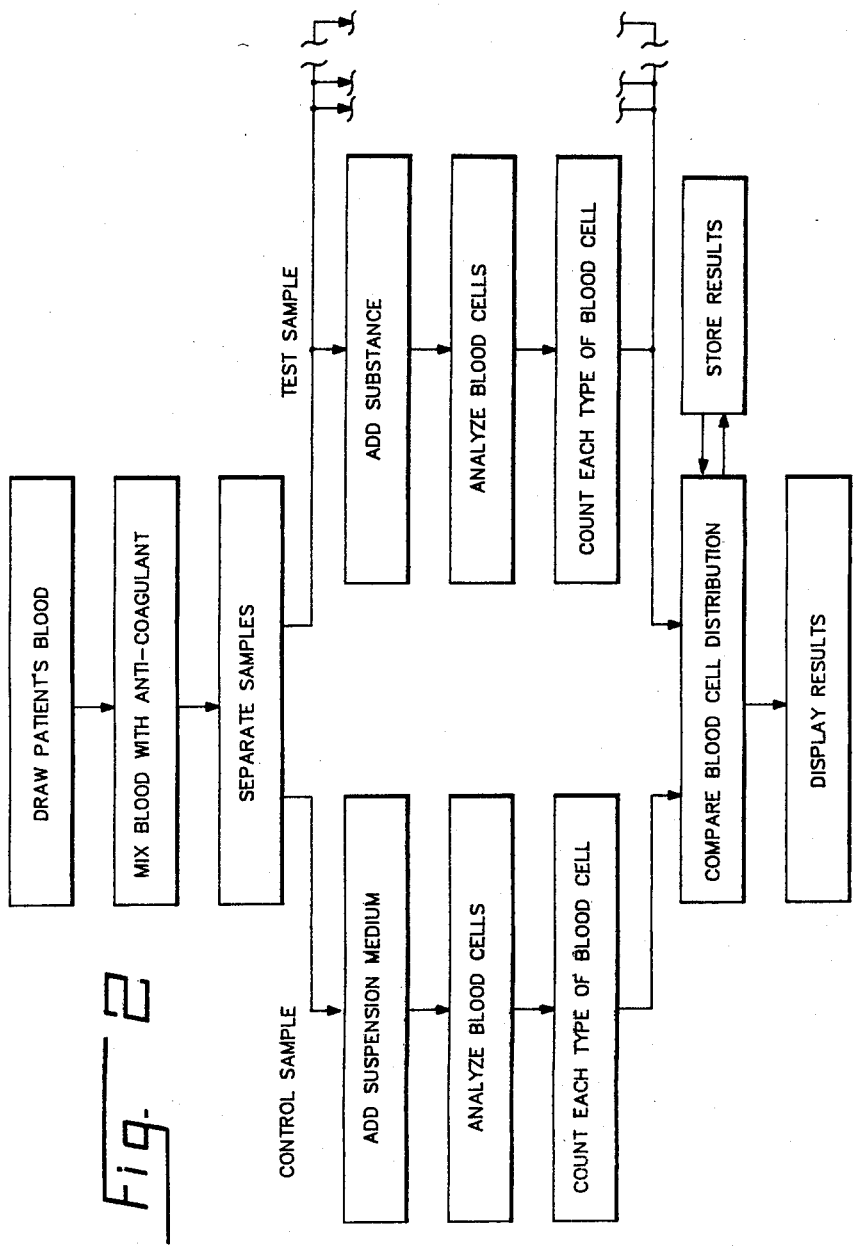

METHOD AND APPARATUS FOR MEASURING THE DEGREE OF REACTION BETWEEN A FOREIGN ENTITY AND A SUBJECT'S BLOOD CELLS

CROSS-REFERENCE TO RELATED APPLICATIONS

This application is a continuation-in-part application of my co-pending applications, Ser. No. 547,767, filed Nov. 1, 1983, Issued as U.S. Pat. No. 4,614,722, on Sept. 30, 1986, and Ser. No. 902,313, filed Aug. 28, 1986.

BACKGROUND OF THE INVENTION

This invention relates to the field of cellular immune reactions; and, more particularly, to a method and apparatus for the direct and/or indirect determination of the degree of reaction (if any) between a foreign entity and a subject's blood cells, for diagnosing a malady of the subject.

Diagnosing maladies is perhaps the single most important aspect of medicine. The key to diagnosing a malady is based on an understanding of the malady's cause.

Many illnesses and afflictions (i.e. maladies other than illnesses, such as an allergy or cancer) are caused by an individual's coming into contact with foreign entities, such as environmental chemicals, including known or possible carcinogens, other toxins or micro-organisms, including viruses and bacteria.

Every day, the human body is exposed to many types of foreign entities, and when so exposed, the body may ingest some foreign entities, by eating or breathing them in, or perhaps merely by touch. Once a foreign entity is ingested, the body identifies it either as being neutral, in which case the body does not react in any extraordinary fashion, or identifies it as being potentially harmful, in which case the body acts to defend itself.

If the foreign entity is in fact harmful, such as a carcinogen or a virus, it will cause certain ill effects to the individual, such as disease. However, even if the foreign entity is benign, and might not cause any untoward effects by itself, the reaction of the body to its identification as being harmful may have its own set of ill effects, such as an allergic reaction.

The body's defenses, primarily the immune system, and the manner in which they act to defend the body, have been greatly studied. In broad terms, the white blood cells (leukocytes) in an individual's blood act as the first line of defense against foreign entities classified as harmful. Once a foreign entity is identified as being harmful, besides the natural (innate) immune response, the body may produce specific antibodies which combine with the foreign entity and, in conjunction with the leukocytes, destroy the invading foreign entity.

I have observed three different steps in the response of the leukocytes to a foreign entity identified as harmful, after the antibodies and leukocytes combine.

First, the leukocyte increases in volume, to surround and enclose the foreign entity. This reaction is similar or identical to a phagocytosis reaction, in which a cell ingests a particle, Bellanti, J. A., Immunology III, W. B. Saunders Co. (1985). p. 16.

Second, after the foreign entity is enclosed by the leukocyte, the volume of the leukocyte decreases in a so-called complement reaction, i.e. the leukocyte develops a small defect in its cell membrane, and begins to extrude a portion of its cellular material, Bryant, N. J., Immunohematology, W. B. Saunders Co. (1982), pp. 54–55.

Finally, the leukocyte releases all of its cellular material, and breaks up its outer membranes. This reaction is similar to the degranulation of basophiles noticed in the presence of IgE mediated reactions, Bellanti, supra., p. 252.

I have recently discovered that some red blood cells and some platelets also participate in the body's immune response to an invading substance, undergoing reactions similar to those of the leukocytes. This phenomenon has not heretofore been recognized, and its discovery may assist in the understanding of the body's immune reactions.

Many theories exist as to the precise mechanism behind the operation of the immune system, i.e. how blood cells recognize and define harmful foreign entities, and how antibodies are produced, etc. No currently known theory, however, explains all aspects of the body's defensive reactions. In addition, no currently known theory is generally accepted as the sole basis for explaining the reactions.

This lack of an understanding of the immune system response has hampered efforts to devise a uniform and comprehensive diagnostic tool or method for the diagnosis of a wide spectrum of maladies. Since a comprehensive understanding of the mechanics of the immune response is lacking, there is no comprehensive understanding of how maladies may be recognized at an early stage.

Currently, diagnosis of a malady is more or less by a look-up method. A subject approaches a doctor and relates his symptoms. The doctor then matches those symptoms with the symptoms of known maladies, and attempts to cull a short list of possible causes from all of the conceivable causes. Based on this list, the doctor will periorm tests to isolate the cause of the malady. If there is no positive test result, then a new series of tests will be performed, and this procedure continues until a positive result is attained. This may take a great deal of time and expense, and some of the tests performed may be discomforting or even painful for the subject.

This procedure is necessary because most tests are directed to specific symptoms of an illness. For example, an illness which affects kidney function may be indicated by an increased level of urea in the subject's bodily fluids. The test, then, for that kidney ailment, would be to check the level of urea in the subject's bodily fluids. Such tests do not identify the malady per se, but rather measure an expected bodily response to the malady's presence.

The look-up method has many drawbacks, however. First, it depends upon the subject's ability to recognize symptoms. If the subject has not started to feel the effects of the malady, then he may not know enough to tell the doctor of a minor symptom which would indicate a serious malady. It is for this reason that a wide battery of tests is often prescribed for a new subject, to ascertain to the extent possible what may be ailing that subject.

These tests may be time-consuming, expensive and even painful. Additionally, if the right tests are not called for, someone may be diagnosed as being in good health, but in fact have a massive tumor (for example) which has not yet begun to cause any visible symptoms. If a subject is suffering from more than one malady, the various symptoms may also mask or disguise each other, leading to a false diagnosis.

A different problem arises if two maladies have similar symptoms. A diagnosis based on symptoms may be unable to discern two completely different maladies having similar symptoms.

Furthermore, the subjectivity of an individual as to the experiencing or relating of certain symptoms may also come into play. For example, a slight headache may not cause an individual any great concern, but may in fact indicate a brain tumor.

An incorrect and possibly fatal diagnosis is always a serious concern to doctors, and there is a serious need for an objective test which may be used to diagnose a variety of maladies, without the possibility of masking or disguising of symptoms, and which may be performed effectively, relatively inexpensively, objectively, and quickly.

Further complicating this situation is the possibility that a particular malady may not cause any noticeable symptoms until it has become quite serious. Thus, the afflicted individual may not know enough to have tests performed.

The test described in my first above-referenced Patent assists in the diagnosis of allergies by a simple blood test. That Patent, however, does not disclose any applicability of the test disclosed therein beyond allergies.

Furthermore, prior tests are not useful in diagnosing maladies for which there are no antibodies produced by the subject. If the introduction of the foreign entity to the body does not result in the production of antibodies specific to the foreign entity, then the body will not react to attack it and no reaction will take place. This is the case, for example, with respect to carcinogens. Since the body may not produce any natural antibodies specific to the carcinogen, the body may not act to attack it. Thus, a cancer caused by the carcinogen is free to develop unfettered, until it is of a size sufficient to be detected by other conventional means, such as by palpation or X-ray. No early detection is possible, however, until symptoms are evident. In many instances, the onset of symptoms means imminent death.

There is thus a need for an objective test which may be used to diagnose a wider variety of maladies, and which may be used to diagnose maladies caused by the ingestion of foreign entities for which no antibodies are produced by the subject. There is also a need for a method of diagnosis in which maladies may be diagnosed at a stage before the onset of externally observable symptoms.

My second co-pending application discloses a test wherein the white blood cells of the subject are sampled to determine the presence of a malady, no test is shown for testing the subject's red blood cells. This test therefore does not assist in diagnosing maladies which affect the red blood cells directly, such as anemias, and offers no suggestion for diagnosis by testing the red blood cells or platelets.

There is therefore still a need for a test which may be used to assist in the diagnosis and treatment of maladies which affect the red blood cells or platelets of a subject.

OBJECTS AND SUMMARY OF THE INVENTION

It is thus an object of the invention to provide a method and an apparatus for the objective determination of the degree of reaction between a foreign entity and the blood cells of a subject.

It is a further object of the invention to provide such an improved method and apparatus where accuracy and reliability will not depend upon the subjective interpretation of symptoms by a subject or his physician.

It is another object of the invention to provide a comprehensive testing method and apparatus which may be used for the diagnosis of a wide variety of maladies, without the need for a multiplicity of tests and procedures.

It is a further object of the invention to provide a method of diagnosis which is capable of diagnosing maladies caused by foreign entities for which the body of a subject produces no antibodies.

In accordance with these and other objects of the invention there is provided a method for diagnosing the presence or absence of a malady in a subject, the method comprising the steps of: counting a number of blood cells of a single type selected from the group consisting of leukocytes, red blood cells and platelets, in a first blood sample drawn from the subject; mixing a substance having a predetermined relationship with the malady with a second blood sample drawn from the subject to form a mixture, and thereby allow blood cells of the second blood sample to react with the substance; counting a number of unreacted and reacted blood cells in the mixture; comparing the number of the blood cells counted in the first blood sample with the number oi unreacted and reacted blood cells counted in the mixture, to determine if the blood cells in the second blood sample reacted with the substance, thereby diagnosing the presence or absence of the malady in the subject.

In accordance with a preferred embodiment of the invention, there is further provided a method for diagnosing the presence or absence of a malady in a subject having blood, the blood including blood cells of at least one of red blood cells, leukocytes and platelets, the method comprising the steps of: separating a sample of the blood of the subject into a control sample and at least one test sample, each of the control sample and the at least one test sample having approximately equal distributions of blood cells therein; counting a number of a first type of blood cells in the control sample; lysing at least a portion of the blood cells in the control sample; counting a number of a second type of blood cells in the control sample; mixing a substance with a predetermined relationship to the malady with the at least one test sample, thereby producing a mixture; counting a number of a first type of blood cells in the mixture; comparing the number of the first type of blood cells in the mixture with the number of the first type of blood cells in the control sample, thereby producing a first result; lysing a portion of the blood cells in the mixture; counting a number of a second type of blood cells in the test sample; comparing the number of said second type of blood cells in the mixture with the number of the second type of blood cells in the control sample, thereby producing a second result, whereby the presence or absence of the malady may be determined by the first and second results.

In accordance with a second preferred embodiment of the invention, there is further provided a method for diagnosing the presence or absence of a malady in a subject having blood, the blood including blood cells of at least one of red blood cells, leukocytes and piatelets, the method comprising the steps of: separating a sample of the blood of the subject into a control sample and at least one test sample, each of the control sample and the at least one test sample having approximately equal distributions of blood cells therein; counting a number of platelets in the control sample; counting a number of red blood cells in the control sample; counting a number of leukocytes in the control sample; mixing a substance with a predetermined relationship to the malady with the at least one test sample, thereby producing a mixture; counting a number of platelets in the mixture; comparing the number of platelets in the mixture with the number of platelets in the control sample, thereby producing a first result; counting a number of red blood cells in the mixture; comparing the number of red blood cells in the mixture with the number of red blood cells in the control sample, thereby producing a second result; counting a number of leukocytes in the mixture; comparing the number of leukocytes in the mixture with the number of leukocytes in the control sample, thereby producing a third result, whereby the presence or absence of the malady may be determined by the first, second and third results.

In accordance with a third preferred embodiment of the invention, there is further provided a Briefly stated, the invention is directed to a method for the diagnosis of a malady in a subject by the observing of a degree of reaction between all blood cells: red blood cells, leukocytes and platelets; in the subject's blood with a foreign entity having a predetermined relationship with the malady being diagnosed. The test includes comparing amounts and sizes of red blood cells, leukocytes and/or platelets in a control sample and at least one test sample. The test sample includes a portion of the subject's blood and the foreign entity being tested.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 1 is a block diagram showing the connection of the various components which make up the present inventive apparatus; and FIG. 2 is a flow chart showing the steps of the inventive method.

DETAILED DESCRIPTION OF THE PREFERRED EMBODIMENT

My first referenced Patent, describes a test for use in the diagnosis of allergies by measuring the degree of reaction between the leukocytes in a subject's blood with a suspected allergen. The disclosure of that Patent is herein incorporated by reference.

What is not evident from a reading of that Patent, however, is my discovery that many common maladies, and some less common maladies, cause reactions in a subject's blood similar to those resulting from allergies. It is my theory that the reactions of the body's immune system in responding to the identification of an allergen, i.e. a leukocyte engulfing the allergen, enlarging and then extruding its contents, is basically identical to the bodily reactions to the introduction of other foreign entities recognized as being harmful, such as a virus or even a carcinogen. In sum, it is my theory that most maladies may be diagnosed by the observation of the reactions of the body's immune system, specifically, the size-distribution of the leukocytes in two samples of a subject's blood: a control sample which has no foreign entity added thereto, and a test sample which has at least one foreign entity added thereto.

The basic method and apparatus of the invention disclosed herein is contained in my earlier Patent, but the breadth of its applicability is significantly wider than heretofore realized, in its reach beyond merely diagnosing maladies other than allergies.

My second referenced Patent application teaches the broad applicability of the basic test to a wider range of tests, and that disclosure is also incorporated herein by reference.

What I have recently discovered, however, is that certain red blood cells and some platelets react to an invading foreign entity in the same fashion as do leukocytes, i.e. they combine with antibodies to react with foreign entities, causing the lysing of red cells. The discovery of this bodily process may, for example, assist in the diagnosis and treatment of anemias, which may be broadly defined as maladies in which a subject has a low red blood cell count.

For example, if a subject has a low red blood cell count due to an allergic reaction to certain foreign entities, then the avoidance of those foreign entities may lead to a normal red blood cell count. The testing for such a reaction by a subject's red blood cells may be performed along lines generally similar to those of my earlier tests.

Furthermore, similar results by testing platelets may be achieved for other maladies. More research is required for determining which types of blood cells are best used to test for certain maladies, but the discovery that all blood cells react in an allergic-type reaction to the presence of an invading foreign entity leads to the importance of testing all types of blood cells for reaction with the foreign entity. For ease of reference, the term "blood cells", as used herein is meant to include platelets, red blood cells and leukocytes, even though platelets are not generally considered to be blood cells for all purposes.

An apparatus in accordance with my invention for performing the tests of the inventive method, as shown generally at 10 in FIG. 1, comprises a counter 12, an analyzer 14, a computer interface 16 and a computer 18, each connected in series, and a disc 20, a printer 22 and a video display 24, each connected to the output of computer 18.

To commence the operation of the inventive apparatus (generally described in the flow chart of FIG. 2) a blood sample is first drawn from the person being tested (subject). Preferably, 10 cc of oxylated blood is drawn from the subject, using sodium citrate as an anti-coagulant (i.e. the blood is stored in blue top B-D brand vacutainers) to prevent clotting of the blood during the test. This single sample may be used to perform a wide variety of tests for a vast array of different maladies.

It is necessary to secure an even cellular distribution of blood cells over the entire volume of the blood sample, and so it is necessary to transfer blood from the vacutainer to an apparatus (not shown) which will have the capability of continuous flow circulation, in known fashion. Such a device will cause the cells of the sample to be distributed generally evenly over the entire sample.

It is preferred that a single blood sample drawn from the subject be used during a battery of tests for a number of foreign entities, and so the blood drawn from the subject is separated into a plurality of smaller samples for testing. The preferred method of separation is to place 100 microliters of the drawn blood into a receptacle containing an appropriate suspension medium, e.g. one-half ml of a balanced pH saline solution. The precise amount of the suspension medium used is not critical, except that the same amount thereof should be used throughout the test, i.e. in each sample of the same blood. This will ensure that measurements taken for the test and control samples may be directly compared by virtue of the fact that they both have a similar number of leukocytes and volume.

The ten cubic centimeters of drawn blood prepared as described will be suitable for approximately 75 tests.

After separation of the drawn sample into the control and test samples, the foreign entities are introduced into the test samples in the form of solutions.

Suitable solutions may be purchased commercially from any one of a number of suppliers. Alternatively, suitable solutions may be prepared by adding 100 mg of a dried extract of that foreign entity to 10 ml of Isoton II or III (distributed by Coulter), or any mixture thereof, or in 10 ml of a suitable diluting solution. In many instances, injectable paragen-free, sterilized water will be suitable, in others perhaps alcohol. The particular diluting solution selected will depend upon the foreign entity being mixed, and the selection of an appropriate diluting solution is well within the knowledge of those of ordinary skill in the art. Once made, the mixture is allowed to stand for 24 hours at room temperature, and then filtered through a mesh capable of filtering solid particles.

Different solutions of foreign entities are introduced into the various test samples. It is preferred that one foreign entity be introduced into each test sample, but it is contemplated that, in some embodiments, each test sample may have a wide variety of foreign entities introduced thereto so that a single drawn blood sample, which may otherwise be usable only for 75 tests, may be used over a much broader range of possible foreign entities. In such embodiments, a positive reaction (described below) for any group of foreign entities would require a subsequent test or tests to determine which of the multitude of foreign entities contained in that test sample was the specific foreign entity which caused the positive reaction. It is also preferred that an amount of the suspension medium, equal to that introduced to the test samples, be added to the control sample. This allows the direct comparison of the two samples, since they will have generally identical counts of leukocytes (before the studied reaction), and generally similar volumes.

At this point, each sample, i.e. the control sample and each test sample, will contain a mixture of suspension medium and whole blood, which in turn includes leukocytes, red blood cells and platelets. In addition, the test samples will have the solutions of foreign entities therein. Since all three types of blood cells are of importance to this test, it is important that each be measured separately.

In the preferred embodiment, counter 12 is Coulter Counter Model Z-M, which may be set to count the number of particles within a given size range. Thus, since platelets are much smaller than red and white blood cells, it is simple to avoid counting them by setting the minimum particle size at a size greater than that of platelets, and less than that of the red and white blood cells, for example 3.5 microns. Similarly, it is simple to count only those cells by setting the maximum level of counter 12 to a similar level.

No such simple method of counting red and white blood cells is presently available, however. It is possible to separate these cells in known mechanical methods, although this method is time consuming.

A preferred method utilizes the fact that red blood cells exist in human serum in a ration of 1000:1 to leukocytes. First, then it is preferred that the red blood cells be counted. This may be taken as a straight count, since the relatively small number of white blood cells existing in blood serum may be disregarded when the count is made. The small error which may occur may be disregarded (on the order of 0.1 per cent), since that is generally far smaller than the error factor of the equipment, and is also far smaller than the amount of change expected in the case of a positive reaction. After the red blood cells are counted, then it is desired to count the leukocytes.

To avoid counting red blood cells, which are of roughly comparable size to the leukocytes, it is preferred that those cells be eliminated. This is preferably accomplished by adding a substance which will immediately cause red blood cells to disintegrate (a "lysing" substance), for example a solution comprising one percent Saponin (Coulter) and the remainder bacteriostatic water. Alternatively, the red blood cells may be mechanically removed from the sample. This solution may also serve to lyse some reacted leukocytes in the test sample, thereby enhancing the observable effects of the reaction (if any) between the leukocytes and the foreign entity (together with the antibodies). After the red blood cells and a portion of the reacted leukocytes are eliminated, preferably after a period of about 30 seconds after introduction of the lysing agent, and counter 12 is set to the predetermined minimum size level, counter 12 may be used to count and size the leukocytes of the control sample. The results of the counting and sizing of the control sample are used as a reference for comparison of the results of the same counts performed on the control samples. It will be appreciated that the platelets may be counted either before or after the counting of the red blood cells but before the leukocytes. Since platelets are not directly affected by the lysing substances, the order of counting the platelets and red blood cells is a mere matter of choice. However, the red blood cells, when lysed, may create particles which are of a size on the order of platelets, so the platelets should be counted prior to lysing the red blood cells, which means prior to counting the leukocytes. Of course, if some other manner of separating the three types of blood cells is used, such as mechanical separation, the the order of counting is even more a matter of mere choice.

If the blood cells in one or more of the test samples react to the presence of any foreign entity, then they will react in the manner described, i.e. by getting larger, then breaking up and finally dissolving. These reactions will cause a distortion of the size distributions of the blood cells in the positive test samples, since the number of blood cells in lower volumetric size ranges will diminish, and the number of blood cells in higher volumetric size ranges will increase, thereby producing a shift in the size-distributions of the counted blood cells.

The output of counter 12 may be read visually, to determine if the number of blood cells in the test sample is less than that of the control (indicating positive reaction) or it may be input to analyzer 14, such as the Coulter Channelyzer, to obtain cellular population distributions of the number of red blood cells present in each of a plurality of size-distribution ranges. This is referred to as "sizing".

The output of analyzer 14 may also be input to computer 18 through interface 16, in known fashion, to store the data and compare automatically the results of the count of each test sample to that of the control sample as well as the size-distribution of the blood cells. If the number of blood cells in a test sample is less than that of the control by more than the error factor of counter 12, then there is a positive reaction. The error factor of each piece of equipment used is readily available from its manufacturer, and may vary from manufacturer to manufacturer. In addition, if the comparison of the size-distribution results indicate enlargement of blood cells, then there is also a positive reaction. Once all comparisons are made, the output of computer 18 may be displayed by any means desired, such as printer 22 or video display 24, and may also be stored on disc 20 for future reference.

Storing data is useful for later reference on the same subject at a later date. If a control sample of a subject's blood taken at a subsequent time is vastly different from that of a first test, then there may be an indication of a vast change in the state of that subject's immune system. This would suggest further testing to determine the cause of such a change.

It is here noted that the above description was made based on the assumption that a foreign entity is added to the test samples to produce thereby a reaction. This may not be effective in all instances. Certain non-immunologic reactions cause cellular reactions similar to the above-described immunologic reaction. In such cases, the inventive test is still effective in diagnosing the malady, so long as the non-immunolgic reaction causes changes in cellular size, or cellular destruction.

As described thus far, the inventive test requires the presence of two elements in the blood: antibodies and blood cells, so that the introduction of the third component of the studied reaction, the foreign entity, will cause the measured reactions to occur. Not all individuals produce antibodies appropriate for all foreign entities, however. This is particularly true for carcinogens, for which no naturally occurring antibodies are present in the blood of most people.

The test will still work, however, with one modification. Instead of adding the foreign entity to the control sample, a diifferent substance, such as an antibody, is introduced thereto. This modification will enable the diagnosis of a malady caused by the ingestion of a foreign entity by the subject, even if the subject does not produce the antibodies on his own. The addition of the antibodies to the test sample completes the requirement that all three components of the reaction: antibodies, foreign entity and blood cells, be present in the test sample.

For example with respect to the testing for a specific cancer, if the carcinogenic foreign entity is present in the subject's blood, the introduction of a monoclonal antibody specific to that carcinogenic foreign entity will enable the blood cells in the subject's blood to attack the carcinogen, and the normally observed reaction will take place.

So long as an antibody is known for any specific foreign entity, the malady caused by the ingestion of that foreign entity may be diagnosed.

In this fashion, it may be objectively determined if the subject has a reaction to any of the tested foreign entities, and is therefore suffering from any of the tested maladies. Such a test may be used to test for any malady affecting the immune system, from influenza, to AIDS, to cancer. Any such malady may be tested for, and at a stage where treatment will be most effective, i.e. at as early a stage as possible.

The discovery that red blood cells react to the presence of certain entities may also lead to a course of treatment for certain anemias, wherein those foreign entities which cause reactions in the subject's red blood cells are removed from the subject's environment, thereby removing a possible cause of depletion of the subject's red blood cells.

It is also here noted that there is nothing in this description which will limit the application of this method to the human immune system. It is believed that this method is equally applicable, for example, in the field of veterinary medicine for any animal having an immune system.

As will be readily apparent to those skilled in the art, the above description represents the preferred, but nonetheless illustrative, embodiment of the invention, which may be realized in other specific forms without departing from its spirit or essential characteristics. For example, the entire apparatus may be automated so that once the sample of blood is drawn from the subject there need be no further human intervention or action until the results are complete. Therefore, the full scope of such invention is to be measured by the appended claims, giving thereto the full range of equivalence which comes within the meaning and range of the claims.

I claim:

1. A method for diagnosing the presence or absence of an immune response indicative of a malady in a subject, said method comprising the steps of:
    counting a number of blood cells of a single type selected from the group consisting of red blood cells and platelets, in a first blood sample drawn from said subject;
    mixing a substance having a predetermined relationship with said malady and eliciting a cellular immune response with a second blood sample drawn from said subject to form a mixture, and thereby allow blood cells of said second blood sample to react with said substance;
    counting a number of unreacted and reacted blood cells of said single type in said mixture; and
    comparing said number of said blood cells counted in said first blood sample with said number of unreacted and reacted blood cells counted in said mixture, to determine if said blood cells in said second blood sample reacted with said substance, thereby diagnosing the presence or absence of said malady in said subject.

2. The method of claim 1, wherein said counting a number of blood cells of at least one of said first blood sample and said mixture is performed by counting a number of blood cells within each of a plurality of varying size-distribution ranges.

3. The method of claim 2, further comprising the step of:
    producing a graph showing said number of blood cells counted in each of said plurality of size-distribution ranges.

4. The method of claim 1, further comprising the step of:

lysing a portion of any red blood cells present in said first blood sample prior to counting said number of blood cells therein.

5. The method of claim 1, wherein said substance is an antibody.

6. The method of claim 1, wherein said substance is a foreign entity.

7. The method of claim 1, wherein said single type of blood cells are platelets.

8. The method of claim 1, wherein said single type of blood cells are red blood cells.

9. A method for diagnosing the presence or absence of an immune response indicative of a malady in a subject having blood, said blood including blood cells of at least one of red blood cells, leukocytes and platelets, said method comprising the steps of:

separating a sample of said blood of said subject into a control sample and at least one test sample, each of said control sample and said at least one test sample having approximately equal distributions of blood cells therein;

counting a number of a first type of blood cells in said control sample;

lysing at least a portion of said blood cells in said control sample;

counting a number of a second type of blood cells in said control sample;

mixing a substance with a predetermined relationship to said malady and eliciting a cellular immune response with said at least one test sample, thereby producing a mixture;

counting a number of a first type of blood cells in said mixture;

comparing said number of said first type of blood cells in said mixture with said number of said first type of blood cells in said control sample, thereby producing a first result;

lysing a portion of said blood cells in said mixture;

counting a number of a second type of blood cells in said test sample; and comparing said number of said second type of blood cells in said mixture with said number of said second type of blood cells in said control sample, thereby producing a second result, whereby the presence or absence of said malady may be determined by said first and second results.

10. The method of claim 9, wherein said first type of blood cells are platelets.

11. The method of claim 2, wherein said second type of blood cells are leukocytes.

12. The method of claim 9, wherein said first type of blood cells are red blood cells.

13. The method of claim 12, wherein said second type of blood cells are leukocytes.

14. The method of claim 9, wherein at least one of said numbers of cells counted is stored in a memory.

15. The method of claim 14, further comprising the steps of:

collecting a second sample of blood from said subject;

counting a number of blood cells of said second sample; and comparing said number of blood cells with said number of cells stored in said memory, whereby any change in a number or distribution of blood cells in said blood of said subject over time may be discovered.

16. A method for diagnosing the presence or absence of an immune response indicative of a malady in a subject having blood, said blood including blood cells of at least one of red blood cells, leukocytes and platelets, said method comprising the steps of:

separating a sample of said blood of said subject into a control sample and at least one test sample, each of said control sample and said at least one test sample having approximately equal distributions of blood cells therein;

counting a number of platelets in said control sample;

counting a number of red blood cells in said control sample;

counting a number of leukocytes in said control sample;

mixing a substance with a predetermined relationship to said malady and eliciting a cellular immune response with said at least one test sample, thereby producing a mixture;

counting a number of platelets in said mixture;

comparing said number of platelets in said mixture with said number of platelets in said control sample, thereby producing a first result;

counting a number of red blood cells in said mixture;

comparing said number of red blood cells in said mixture with said number of red blood cells in said control sample, thereby producing a second result;

counting a number of leukocytes in said mixture;

comparing said number of leukocytes in said mixture with said number of leukocytes in said control sample, thereby producing a third result, whereby the presence or absence of said malady may be determined by said first, second and third results.

17. The method of claim 16, further comprising the steps of:

lysing at least a portion of said red blood cells in said control sample prior to counting said number of leukocytes therein.

18. The method of claim 16, further comprising the steps of:

lysing at least a portion of said red blood cells in said mixture prior to counting said number of leukocytes therein.

* * * * *